United States Patent [19]
Ross, Jr. et al.

[11] Patent Number: 5,823,948
[45] Date of Patent: Oct. 20, 1998

[54] MEDICAL RECORDS, DOCUMENTATION, TRACKING AND ORDER ENTRY SYSTEM

[75] Inventors: James E. Ross, Jr.; William J. Lynch, both of San Antonio, Tex.

[73] Assignee: RLIS, Inc., San Antonio, Tex.

[21] Appl. No.: 676,458

[22] Filed: Jul. 8, 1996

[51] Int. Cl.⁶ .................................................. A61B 5/00
[52] U.S. Cl. ................................. 600/300; 705/3
[58] Field of Search .................. 128/630, 906, 128/920, 924; 395/202, 203, 924; 600/300; 705/2, 3

[56] References Cited

U.S. PATENT DOCUMENTS

| | | |
|---|---|---|
| 3,566,370 | 2/1971 | Worthington et al. . |
| 3,794,982 | 2/1974 | McCormick et al. . |
| 3,839,708 | 10/1974 | Bredesen et al. . |
| 3,940,742 | 2/1976 | Hudspeth et al. . |
| 3,970,996 | 7/1976 | Yasaka et al. . |
| 4,053,951 | 10/1977 | Hudspeth et al. . |
| 4,085,446 | 4/1978 | Nagamura . |
| 4,130,881 | 12/1978 | Haessler et al. . |
| 4,205,387 | 5/1980 | Ovshinsky et al. . |
| 4,228,506 | 10/1980 | Ripley et al. . |
| 4,260,854 | 4/1981 | Kolodny et al. . |
| 4,346,449 | 8/1982 | Ovshinsky et al. . |
| 4,611,298 | 9/1986 | Schuldt . |
| 4,893,270 | 1/1990 | Beck et al. . |
| 5,146,439 | 9/1992 | Jachmann et al. . |
| 5,553,609 | 9/1996 | Chen et al. .................. 600/301 |

*Primary Examiner*—William E. Kamm
*Assistant Examiner*—George R. Evanisko
*Attorney, Agent, or Firm*—James Creighton Wray; Meera P. Narasimhan

[57] ABSTRACT

The new system provides: automatic incorporation of dictated text; medical records summary generation in medical English text; parsing dictation to data; prephrased text; automatic generation of medical record as consequence of data entry; automatic notation of allergies, significant medical conditions and pregnancy; pregnancy linking, automatically; security card—close on pull; multi-look grease board; outstanding orders listing for all patients in the department; department layout; room selection excludes occupied rooms; nurses notes to text; nurses notes from physician orders to nurses; lab request screen shows all previously ordered labs; therapeutics; ACLS recording; lacerations; doctor specific prescriptions and medication orders; review of systems; coding level alerts; differential diagnosis—filter to sex and age; diagnosis—fractures to text; doctor interval reexamination; patient instructions predicated on what was done; patient instruction video on demand; patient informed consent video on demand; video teleconferencing; electronic signatures; automatic backup and incremental backup with system on-line; critical management reports; and automatic research data extraction.

6 Claims, 7 Drawing Sheets

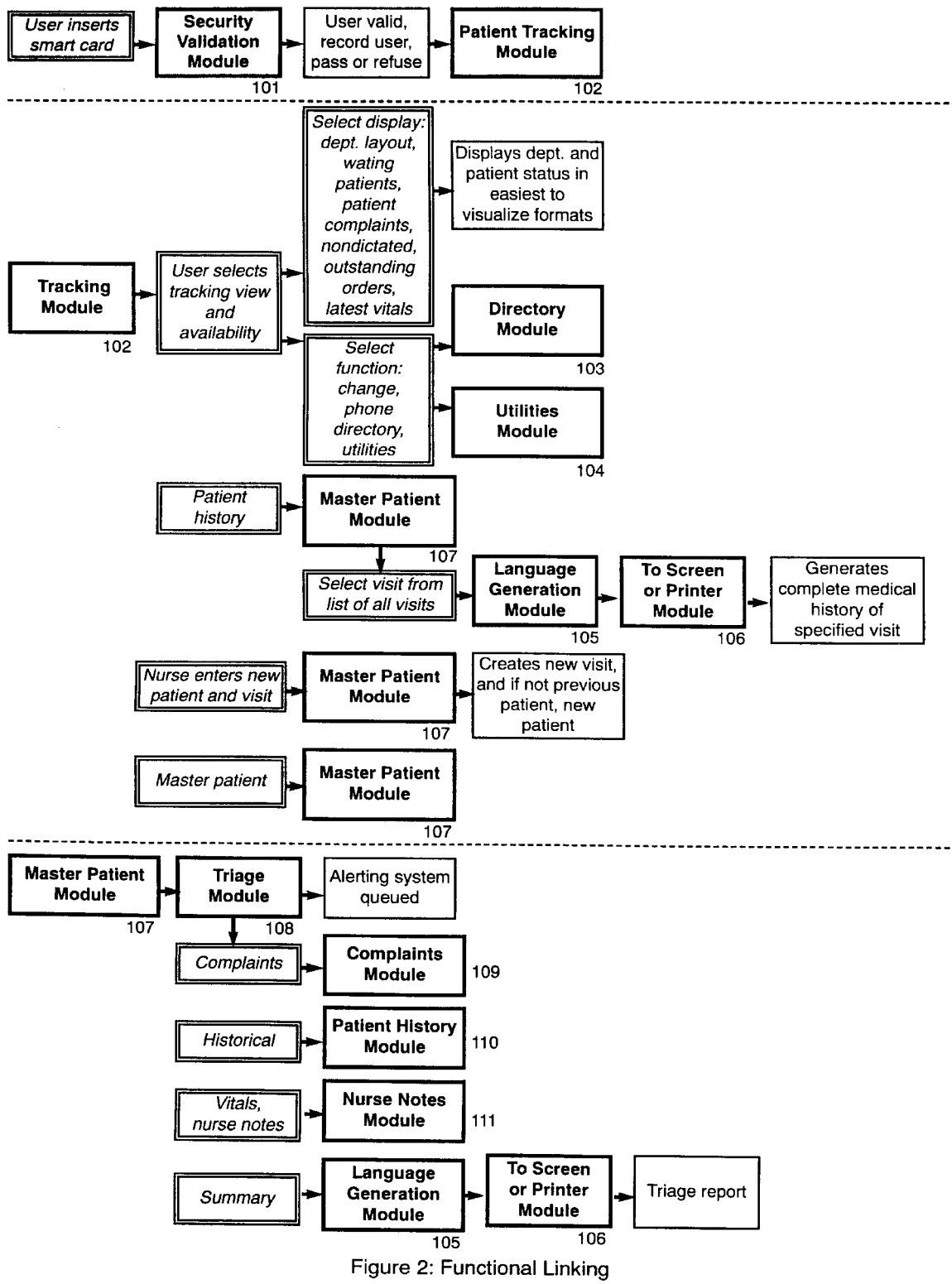
Figure 2: Functional Linking

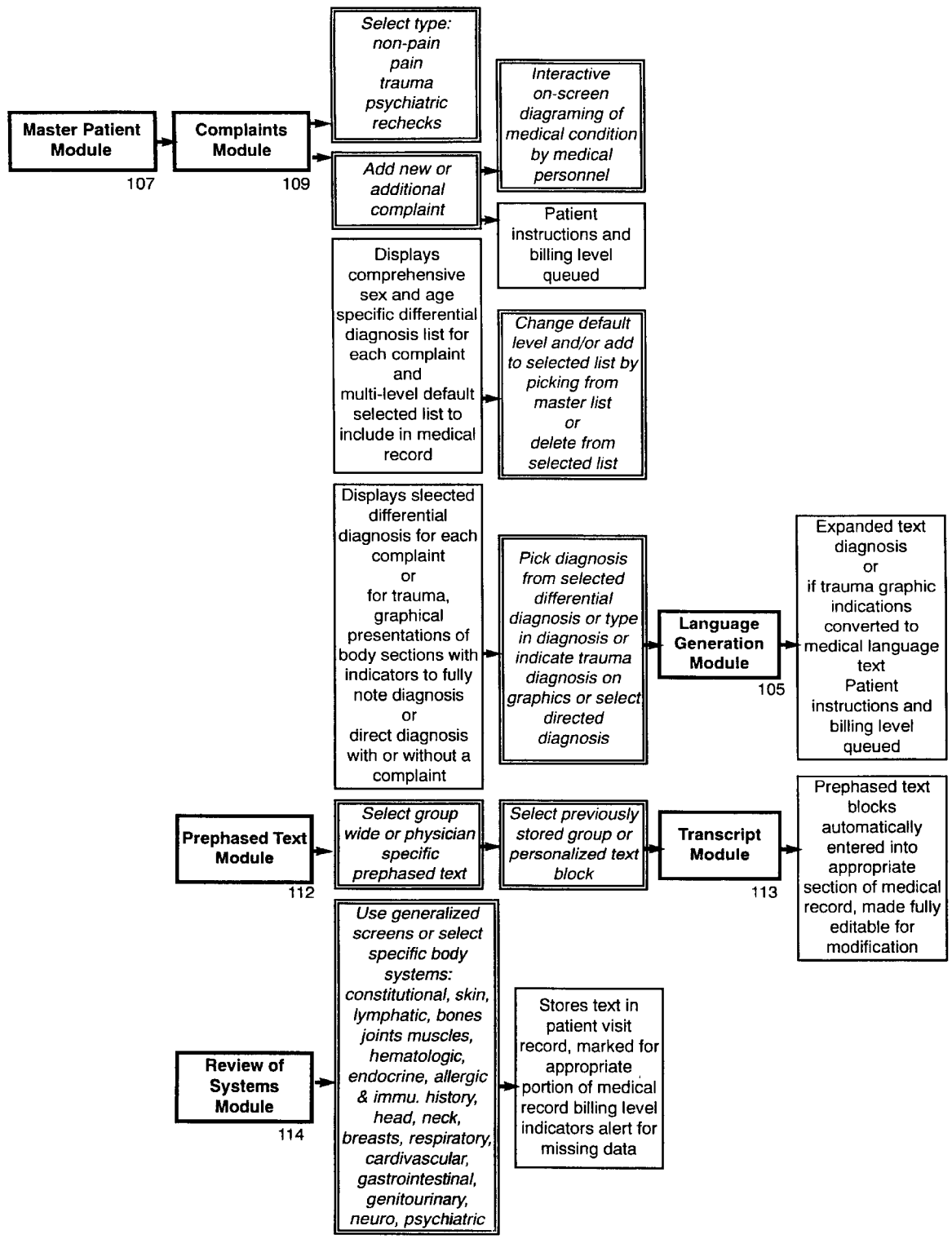
Figure 3: Functional Linking

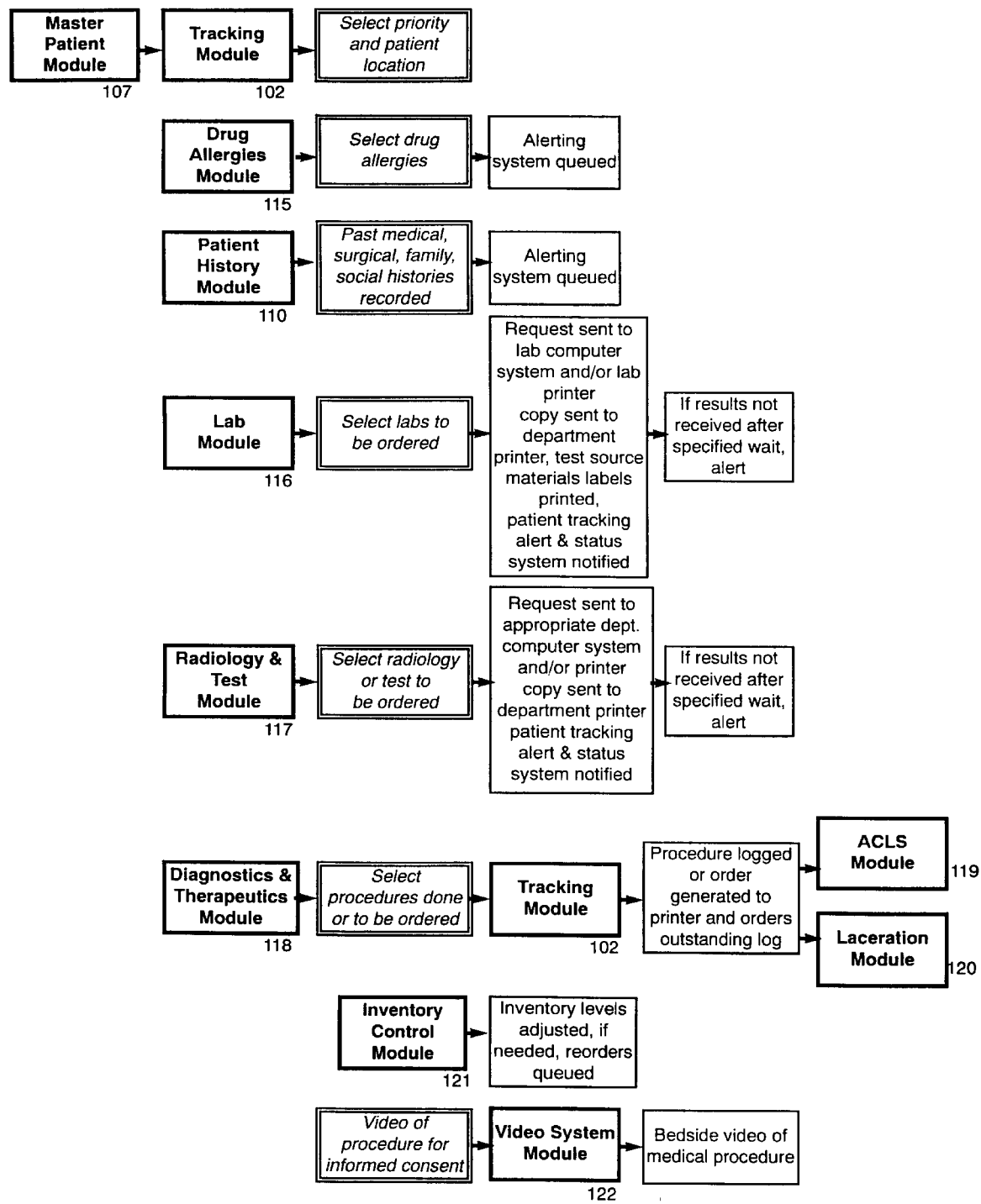
Figure 4: Functional Linking

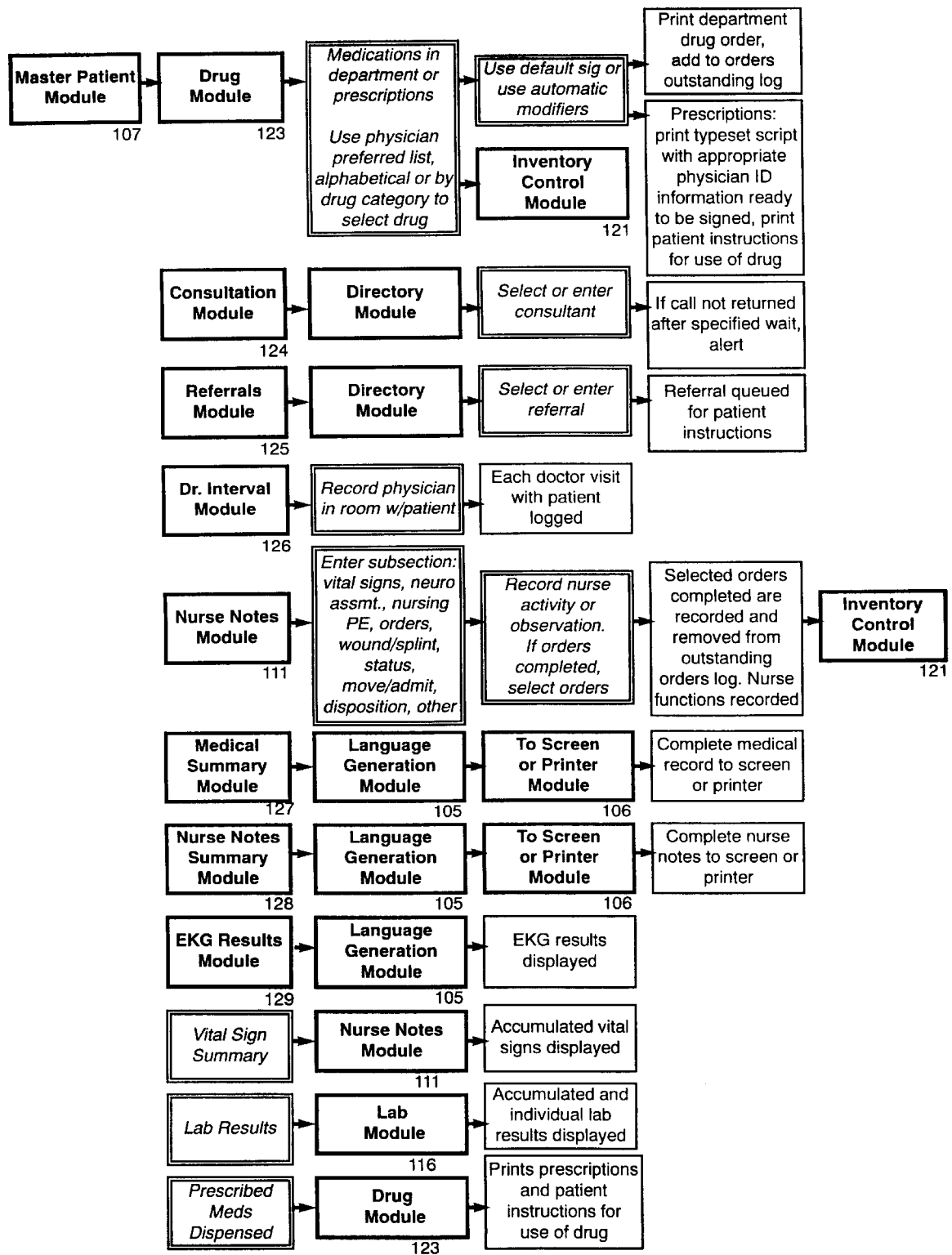
Figure 5: Functional Linking

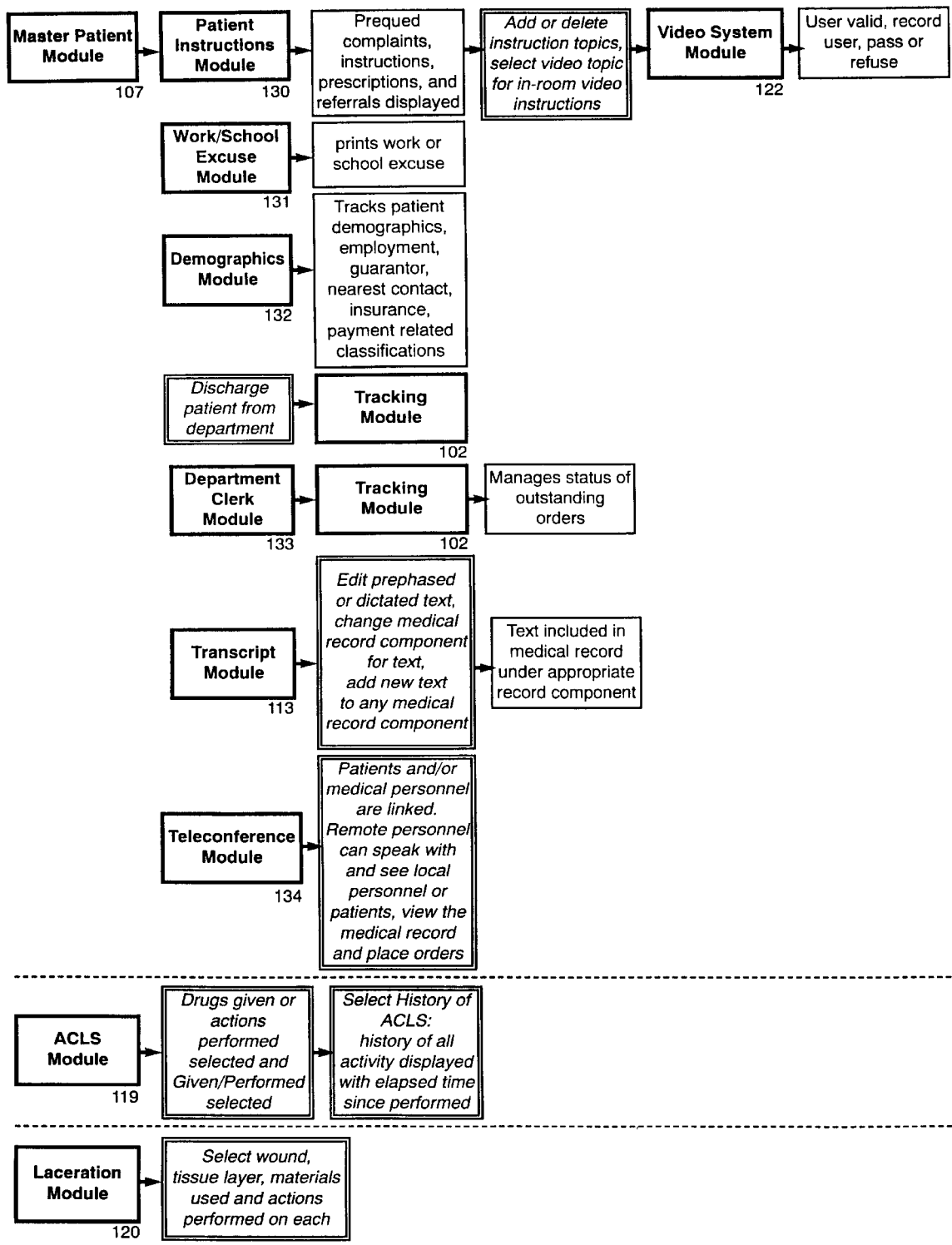
Figure 6: Functional Linking

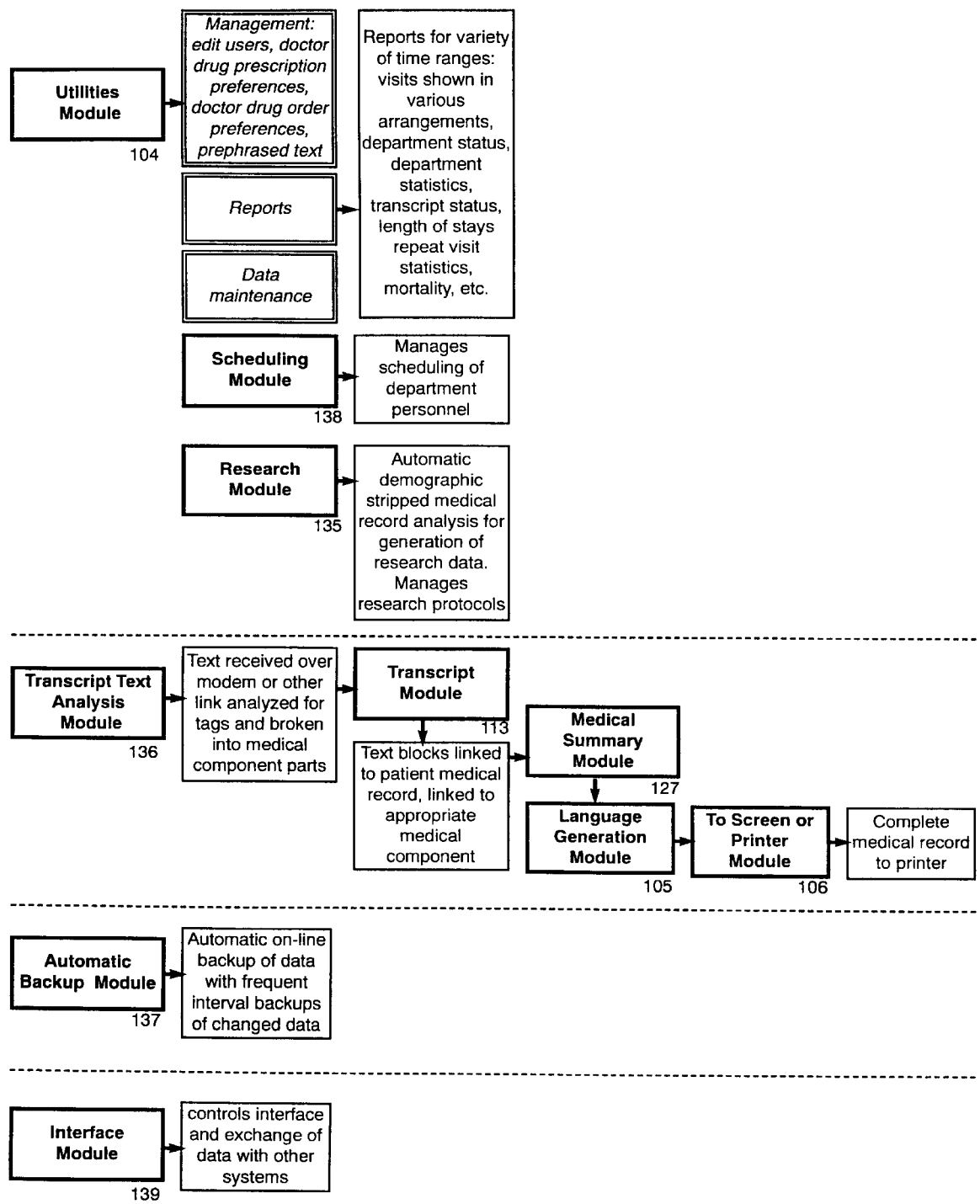
Figure 7: Functional Linking

MEDICAL RECORDS, DOCUMENTATION, TRACKING AND ORDER ENTRY SYSTEM

BACKGROUND OF THE INVENTION

Need exists for immediate triage, reports and medical records which may be generated and supplied to physicians and nurses and which may be translated into patient reports, instructions and prescriptions without delaying or burdening hospital personnel.

SUMMARY OF THE INVENTION

The new system provides automatic incorporation of dictated text; medical records summary generation in medical English text; parsing dictation to data; prephrased text; automatic generation of medical record as a consequence of data entry; automatic notation of allergies, significant medical conditions and pregnancy; pregnancy linking, automatically; security card close on pull; multi-look grease board; outstanding orders listing for all patients in the department; department layout; room selection excludes occupied rooms; nurses notes to text; nurses notes from physician orders to nurses; lab request screen shows all previously ordered labs; therapeutics; ACLS recording; lacerations; doctor specific prescriptions and medication orders; review of systems; coding level alerts; differential diagnosis, filter to sex and age; diagnosis, fractures to text; doctor interval reexamination; patient instructions predicated on what was done; patient instruction video on demand; patient informed consent video on demand; video teleconferencing; electronic signatures; automatic backup and incremental backup with system on-line; critical management reports; and automatic research data extraction.

The new computer system is accurate, comprehensive and fast. The present invention provides accuracy in documentation and speaks the language of medicine. It provides speed in documentation and captures time for every care giver, not just physicians. The new system provides access to the documentation, eliminating constant hunting for the chart.

The invention generates a comprehensive document; a full and complete medical record. The new system provides triage, exit instructions, patient tracking and every phase of the encounter. Security, privacy and integrity of data are maintained. The data is up to date and pertinent. Every facet of medical care is documented. Pharmaceutical, procedural, diagnostic and patient instruction data are current and state-of-the-art. The system is built from the ground up to meet the unique needs of an acute care environment.

Pertinent and comprehensive patient care data are gathered. The patient's old records are organized for review on subsequent visits. Multiple visit patient data is instantly available. The new system allows physicians to confirm that the right questions were asked, the appropriate exam elements were covered, the likely diagnoses were considered, the appropriate treatment was rendered and consultation was made in a timely fashion. The invention reduces medicolegal liability and assures quality of care. Data is organized in a format that meets HCFA criteria for proper billing for care rendered, meets E&M coding criteria and facilitates CPT coding.

Data is accessible and maneuverable. Rapidly retrievable data generates useful management reports. Most information gathered is stored as data, not as text. The invention provides instant access to massive quantities of patient data. Storage techniques are innovative, allowing simultaneous access and input to the same chart. Interface is provided with outside data sources: registration, lab, X-ray, transcription, ancillary services, central supply, pharmacy and the clinical data depository.

The invention enables research and remote analysis by real-time secured remote access to the database by primary and consulting physicians, as well as other hospital facilities. The acquired clinical data is uploaded to central data warehouses for purposes of statistical analysis and research. With strict maintenance of patient-identifying data, privacy and confidentiality are assured.

The new computer system is extremely intuitive and easy to use. It limits disruption due to new personnel coming into the department. Clinical staff like to use it, which increases user satisfaction. Speeding of patient throughput increases patient satisfaction. Meaningful reports are provided to increase productivity in the acute care setting. Individualized user preferences are accommodated with customized text entries. Doctors and nurses need not have world class typing skills to use the system effectively.

Nursing and physician documentation are combined in the final medical record. The system is transparent to the user, not distracting.

The importance of care giver decision making is emphasized, allowing personnel to use common sense on how and when to record information. The new system allows data entry in dependence. A user is not required to fill in every blank before proceeding to the next page. A consistent screen "look and feel" reduces user fatigue, and facilitates speed and accuracy.

T he overall cost of providing care is reduced to remain competitive in the rapidly evolving world of managed care.

Automatic incorporation of dictated text into the computer generated medical record summary: the summary is formatted so as to make it easy for the caregivers (doctors, nurses, clerks, ancillary services personnel, orderlies, paramedical personnel, and other qualified personnel) to read and understand what is going on with the patient. The medical record also has a Specific organization necessary for billing for the care which is rendered. In order to produce a hybrid record in which much of the information is entered by clicking on buttons or check boxes and combine this data with information which is dictated, it is important that the dictation go to the appropriate places in the summary. For instance, a doctor may enter much of the information in the Review of Systems (ROS) by checking boxes. But he may wish to dictate a small unique bit of information which is not present in the ROS screens. This dictated text is automatically inserted into the record at the appropriate location.

Medical records summary generation in medical English text in a standardized format from the data in the database: the nurses and doctors put patient information into the chart using touch screen, mouse, keyboard, or by dictating to a transcriptionist. This is done on entry screens which have standardized look and feel so as to maintain familiarity with the layout and organization of a very large body of information. This information load cannot be reduced if a comprehensive record is to be produced. When the summary is called up on screen or as a printout, all of the patient data is converted into medical English text and reads as if it had been dictated by a nurse or doctor. This includes the parts which were actually dictated. The summary is generated in under three seconds from thousands of clinical facts which were gathered during the process of patient care. The summary can be called up at any time and will show everything that the medical personnel have input about the patient up to that point.

Dictation: the portions of the medical record which are dictated initially are received by the communications server(s), analyzed for patient and content, attached to the proper patient and visit and broken into its component medical parts. When a medical summary is produced, dictated text is attached to the proper part of the medical record. This allows summaries to include all data including information which was initially entered by dictation.

Prephrased text: these computer system data entry screens allow medical personnel to select prestored personalized text phrases to be included in specific medical record components. This makes including frequently used personalized text very fast. Once added to the record, the text is fully editable.

Automatic generation of the medical record as consequence of data entry: in every aspect of the computer system, information that is input in one place is included in all places that are relevant. Many caregivers provide input of information into a patient's medical record. The input is added at different times from different locations. Some of the data comes from other departments. All of the acquired data is collated into a properly formatted medical record automatically. This may be output to a screen as a summary or printed. If the patient dictation returns after the patient is released from the department, the printed record is generated automatically.

Automatic notation of allergies, significant medical conditions and pregnancy: on all medication entry screens and on screens where a nurse executes an order for medication, pertinent medical conditions are noted to prevent medical complications.

Security card close on pull: the computer system has security measures which limits access to the system. Patients, family members, or others are prevented from looking into medical records or entering information. The caregiver approaches a station terminal and inserts a security card. The local station terminal becomes active. The user is automatically identified and areas in which the user has "rights" are made available. All entries are attributed to the correct user. When entries are complete, the card is pulled from the reader. The computer system stores all entered data and the terminal is returned to a protected state.

Patient tracking: Various displays provide the state of the hospital department indicating patient location, doctor assignment, patient status, and order status.

Nurses notes to text: 95% of all the nurses notes are generated by simple selections on screens in the nurses notes section. Little typing is necessary for producing comprehensive nursing notes. Physician orders are automatically queued for nurses, and can be "picked off" to record the activity in the medical record and indicate completion.

Labs, radiology, and tests can be ordered and results automatically returned to the system.

Therapeutics: a comprehensive selection of therapeutics can be entered as performed or generate orders for others to complete.

ACLS recording: ACLS procedures and observations can be quickly entered as they are performed. At any time, a quick summary of procedures performed with elapsed times can be displayed.

Lacerations: documentation of laceration repair allows for procedures performed on each tissue layers on multiple lacerations.

Doctor specific prescriptions and medication orders in the department: each doctor can have a physician-specific list of medications which are frequently prescribed. Both in-department drug orders and prescriptions can be generated using a physician-specific drug list, alphabetical master list, or category-based list. Generated prescriptions include drug-specific patient instructions in English or Spanish.

Review of systems: the system easily tracks review of system responses, automatically grouping answers into appropriate body system and separating pertinent negatives from positive responses. Body system headlines aid in proper coding for care rendered.

Coding level alerts: when patient complaints are entered, the system indicates to users medical information that should be collected to receive proper coding for billing. As the appropriate information is collected, other indicators so indicate. This assures that all pertinent information is entered into the medical record. It aids in increasing the quality of care rendered and in the coding level which can be attained for the care rendered.

Differential diagnosis: the system automatically generates a comprehensive sex and age specific differential diagnosis based on the patient's complaint(s). A preselected multi-level sublist of the most likely diagnoses is included.

Diagnosis: a diagnosis can be selected from the differential diagnosis, or created using body part graphics to indicate injuries.

Doctor Interval Reexamination: each time a physician visits a patient, the system can document the date/time of the visit.

Patient instructions predicated on what was done: the computer system produces discharge instructions to the patients telling them about their illness or injury, about what was done for them, as well as what they should do to care for themselves at home. Warnings are given to patients to return to the medical facility or seek further care when necessary. The instructions also list referrals. In most circumstances these instructions are entered automatically based on the patient's complaints, diagnoses, and treatment rendered.

These and further and other objects and features of the invention are apparent in the disclosure, which includes the above and ongoing written specification, with the claims and the drawings.

DETAILED DESCRIPTION OF THE PREFERRED EMBODIMENTS

Figure 1:
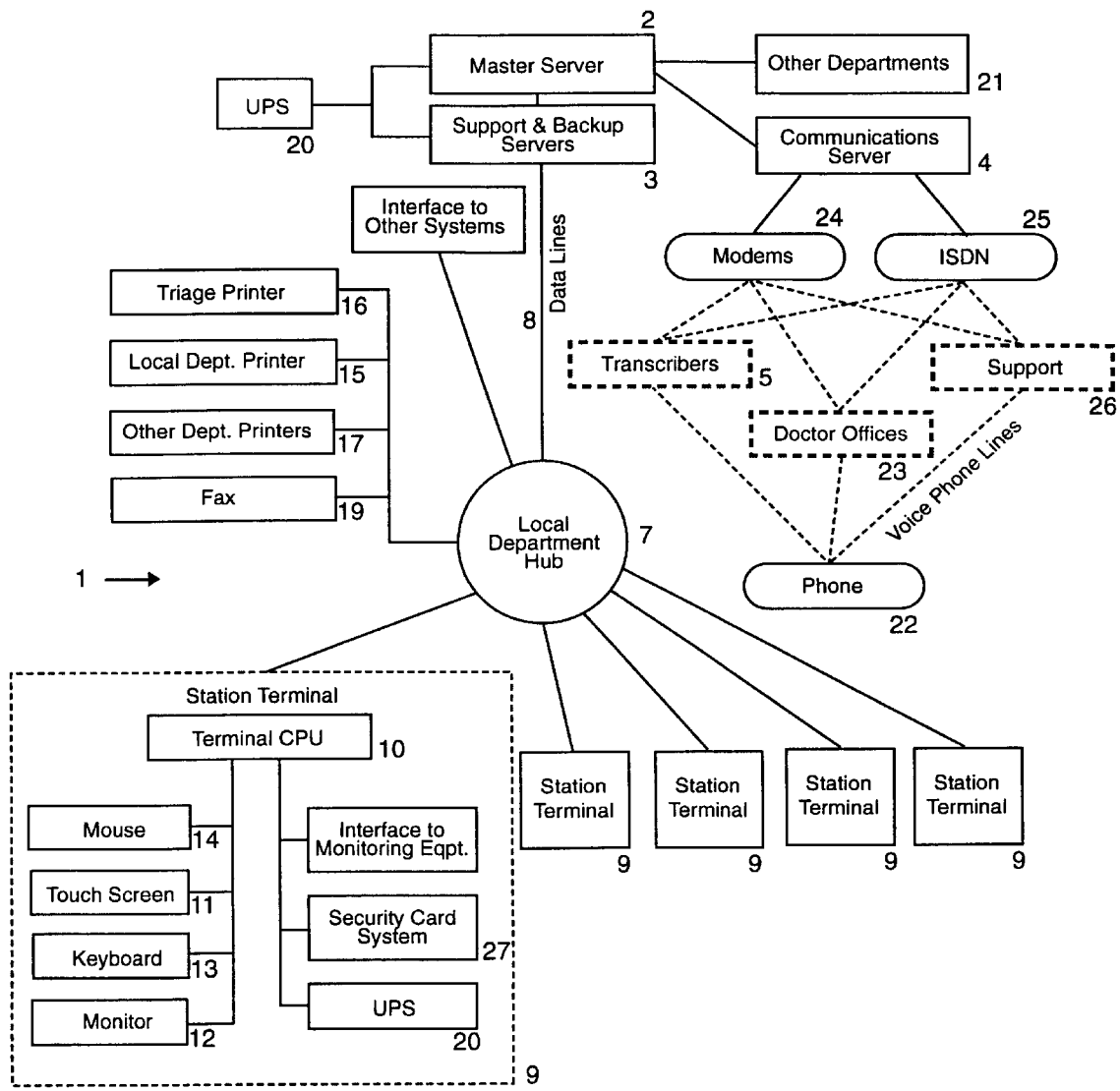
FIG. 1 schematically shows the system network FIGS. 2–7 schematically show functional linking.

A medical records, documentation, tracking and order entry system 1 is shown in FIG. 1. Fault tolerant file servers 2 and support and backup servers 3 use standard disk drives or fully redundant arrays of drives on each server. A communications server(s) 4, linked to each of the file servers, receives incoming transcription 5. A network has a hub 7 connected to the file servers 2 and 3 by data lines 8. Peripheral terminals 9 are connected to the network in a star configuration with the hub. The peripheral terminals 9 have individual central processing units 10 with hard disks. Touch screen 11, monitors 12, keyboards 13 and mouses 14 are connected to the CPU'S. Software resides in the communication server(s) 4, in the dual file servers 2 and 3 and in the peripheral CPU's 10. Patient data is received in the peripheral CPU's via the touch screens, mouses, and keyboards and for storing the patient data in the peripheral CPU's and file servers. A distributed dictation system has inputs adjacent to the CPU'S. A transcription system 5 is connected to the multiple inputs and is connected to the communication server(s) 4. Transcribed dictation is received in the communications server(s) 4. The transcribed dictations are placed in an electronic storage bin in the communications server(s) for transferring the dictation transcriptions to the file servers, and storing the dictation transcriptions in the file servers 2 and 3 as text associated with patient data for particular patients. A printer 15, connected to the network, generates reports on individual patients and management reports of system operations of statistical information, doctor related activities, nursing related activities and patient statistics.

A triage printer 16 in the department prints information about patients' complaints, locations and physician and nurse assignments, and prints lists of patients in the order of immediacy. Other printers 17 may be located in other locations within the department or in other departments. A fax 19 is connected to the network 6 to send printed documents over telephone lines to remote locations.

Uninterruptable power supplies 20 supply power to all the local systems. Other departments 21 are connected to the master server 2 to receive data from other departments and to send data to the other departments.

A telephone system 22 provides communications with remote offices such as doctor's offices 23, and a transcription service which serves transcribers 5. Modems 24 are connected to the communications server(s) 4 for communicating with doctors' offices, transcribers and support from the system suppliers. An ISDN data network 25 is connected in parallel with the modems 24 to connect with the supplier's support 26, the doctor's offices 23 and transcribers 5.

The patient record documentation method provides tracking and order entry. File servers provide data and software from the file servers through a network hub and network to multiple CPU'S. The patient data is transferred from the CPU's to the file servers. Portions of the record that are unique to particular patients are dictated. The dictation is transmitted over voice lines to a transcription center where the dictation is transcribed. The transcribed dictation is transmitted to the communication server(s), which feeds the dictation transcription to the file servers as text components. The text on particular patients is stored in the file server with the tabled data. Word and sentence generation and coordination software is stored in the peripheral CPU'S. Monitors display text sentences generated by the generation software as summaries, together with the text from the dictation transcriptions. The text summaries are sent from the peripheral CPU's to a printer via the local network for generation of printed patient textual reports with sentences generated in medical English text.

Nurses' notes are entered as data on touch screens, mouses and keyboards. The data of nurse's notes is transferred from the peripheral CPU's to the file servers, which stores the nurse's notes information as data. The nurse's notes data is transmitted to the peripheral CPU's, which recompile the data into nurse's notes text, display the nurse's notes as text on the peripheral CPU monitor screens and print the nurse's notes text on the printer.

Prephrased text examples are stored in the file servers. Individual physicians and nurses preliminarily select prephrased text examples as personalized text for compiling with data to produce medical English textual summaries and reports.

Nurse's orders are generated by entering physician orders to nurses at peripheral CPU'S. The physician orders are transmitted as physician orders data to the file servers. Physician orders data are stored with the patient tabled data in the file servers. Physician orders data are provided from the file servers to the peripheral CPU's, which display the physician orders data as textual nurse's orders on the CPU's, print nurse's orders, display all outstanding nurse's orders on the CPU's on request and display all nurse's orders specific to the patient. Entering executions of the nurse's orders on the patient display automatically changes the executed nurse's textual notes for display in summaries.

Patient record documentation tracking and order entry starts with logging on to a peripheral CPU, displaying the user's name and the active patient list "grease board," and showing room location, patient's name and physician, nursing orders, priority and elapsed time of stay, and status of assignment of nurse and physician, ordering of X-rays, labs and tests, nurse's orders, records, dictation and vital signs.

Status is shown in small letters for ordering of X-rays, labs, tests, nurses' orders and dictation, and large letters to indicate completion of X-rays, labs, tests, nurse's orders and dictation transcripts.

Active patient list information is displayed in a department layout.

A screen shows a list of patients waiting to be seen by a physician, in the order of priority. Another display shows patient lists by patient complaints. A further display lists patient lists by those whose charts have not been dictated by the physician.

In FIGS. 2–7 of the drawings, showing the functional linking of the program, the double-line boxes with italic text show actions by users. The heavy line boxes with bold text show program modules. The single line boxes with Roman text show results or output.

Arrows show direct routing.

Moving from left to right across the page, the functions are sub functions or accessed functions from those toward the left. In other words, moving from left to right drills down into deeper functions of the program.

The reference numbers are used to provide additional text detail about the box being referenced. TeleMed denotes the invention.

Broken lines allow the break-up of sections and movement to the left so as not to run out of room moving across the page.

All modules, where appropriate, record data to the medical record with time/date stamps and who performed the function.

101. Security Validation Module—Personnel using the system must clearly demonstrate their identity using a variety of methods depending on the system configuration. Single and multiple passwords, smart card technology, magnetic card or other personal ID technologies. The user's identity establishes the individual "rights" to use various functions. For example, physicians may be the only users given rights to generate prescriptions, nurses could have rights to implement various medical procedures, ward clerks might need rights to order labs, but records clerks may be limited to changing demographic information. When smart cards are used, the system is available only while a proper, authorized card is inserted. Upon withdrawal, the system completes any processes and reverts to a non responding mode.

102. Tracking Module—Medical personnel can quickly see the status of both individual patients and the entire department. TeleMed initially displays an active patient list showing all patients within the department. This display also provides a variety of additional pertinent information such as location, priority, elapsed time since entering the department, order status, vitals status and assigned physician.

This information can be presented in a variety of formats, sometimes with additional information, to help the department personnel quickly obtain the patient tracking information they need. Department layout displays a map of the department showing occupancy (and availability) and physician assignments. Waiting patients shows patients in the order they should be taken. Patient complaints presents patients with their associated complaints. A patient can be selected from any of these displays to enter his/her individual medical record.

Other displays show outstanding orders and the latest vitals on each patient.

This module also controls creation of new visits and, if the patient has never previously visited the hospital, creation of new patient records. New visits can be created without knowing the patient identification. Identification can later be changed here when such information is available.

Historical medical records can be located using a variety of patient information such as name, social security number or previous hospital numbers. Using a name will display all patients with similar names with additional identifying characteristics such as birth date. The specific patient can be selected and previous visits will be displayed with complaints. Selection of a visit provides access to a medical record summary for that visit.

103. Directory Module—Provides a directory of physicians and other services. Can be filtered to physicians with specific specialties and/or managed care affiliations. Physician preferences to be notified if a patient enters the hospital and referral preferences are included.

104. Utilities Module—This sections handles reports, system management, and data maintenance. Management includes editing users, doctor drug prescription preferences, doctor drug order preferences, prephrased text, and other system functions. Reports can be created for any time period. They include department status, department statistics, transcript status, length of stays, repeat visit statistics, mortality, outcomes analysis, etc.

An extensive selection of physician and management reports are available. Since TeleMed stores medical facts as discrete facts rather than text, extensive analysis of an extremely wide variety of medical relationships can easily be accomplished.

A variety of maintenance utility functions are included.

105. Language Generation Module—A key function within the TeleMed program is the language generator. TeleMed stores most medical information as individual specific medical facts rather than as text. When displaying these facts in an on-screen medical summary or on printed medical records, these facts are quickly converted to complex sentence structure similar to physician's dictated medical text.

The language generator builds sentence structure, often containing multiple related facts taken from widely separated points within the program. The program uses a pronoun sequencing technique which produces medical language more like the way medical personnel actually record medical records.

Medical facts are analyzed for responses and type in relation to the patient's sex and age, then converted to initial sentence structure. Where appropriate, the language generator intelligently rearranges the order in which facts were entered to provide the information in a more usable and medically appropriate format. The structure is analyzed and modified if compound sentences can linguistically improve structure. Text such as dictation is analyzed for type and integrated into the previous structure. All text is then analyzed as to the need for headlines and subheads. Needed heads are inserted. The use of bold increased-size headings for major sections and bold or italic subheads allow for quick viewing and easy location of specific facts.

106. To Screen or Printer Module—This module formats text to appropriate output. Manages screen display and movement or manages printer page output.

Output from the language generator module is analyzed and reformatted for the requested output mode (screen or print).

Medical records are printed in a typeset format whereby all medical facts are grouped under the proper medical headings.

The module can automatically fax a copy of the patient's record to the patient's private physician or generate an extra copy of medical records for patients with specific diagnosis or other characteristics for audit.

107. Master Patient Module—Controls routing to all patient-specific screens. Controls specific patient location and priority (passed to Patient Tracking Module). Movement of a patient is noted by a simple selection of available locations (occupied beds are excluded from the selection). Manages billing coding level alerts used to warn medical personnel that the medical record is incomplete to support the level of billing possible based on accumulated facts about the visit. Indicators show what additional information should be collected. Manages master alerting system to warn medical personnel of significant medical conditions.

This module also performs ongoing statistical trend analysis of patient data to alert medical personnel of dangerous long-term trends in the patient's medical condition.

Input and output of liquids and solids by the patient, bed generated patient weight and direct incorporation of monitoring device output are automatically tracked.

Physician electronic signatures can be added to the medical record.

108. Triage Module—This section collects specifics about the medical encounter that pertain to fulfilling legal hospital requirements for triage. Many responses are later intelligently used by the system. Facts such as pregnancy status later cause the system to automatically alert medical personnel as procedures are about to be performed, and warn personnel when orders are given (such as specifying abdominal protection when x-rays are ordered). Upon completion of triage, a triage summary produced by the language generator can be printed.

109. Complaints Module—TeleMed is a complaint driven system. This module manages complaints, differential diagnosis and diagnosis. As complaints are entered, the system begins to automatically modify later functions so department personnel deal with a dramatically reduced array of selections. For example, a comprehensive differential diagnosis is filtered to only those appropriate to the complaint, sex and age, and a recommended multilevel subset (none, light, medium or heavy variations are set by physician preferences) is used as a starting point for physicians to place in the medical record. They can then easily add to or delete from this starting point. Patient instructions relating to a complaint/diagnosis are automatically queued.

When a complaint is selected, an extensive knowledgebase is used by the program to establish parameters the program will follow throughout the rest of the visit. These parameters guide the program in selection of screens (such as to address the appropriate sex), generation of text, billing code levels, order restrictions or enhancements, etc. As the encounter progresses, the parameters are modified by the program to fit new facts collected.

The system can store photos of injuries or conditions taken with a digital camera directly into the patient's medical record.

The final diagnosis(es) can be easily selected from (but is not limited to) the differential diagnosis. Trauma diagnosis (es) can be selected from graphic presentations of the appropriate body parts. For example, a particular fractured bone and the fracture location, characteristics, and type can be indicated on a graphical display of the body part. TeleMed converts the fracture facts into proper medical language describing the injury.

110. Patient History Module—Patient histories and current conditions are collected using a series of screens providing a comprehensive selection of medical facts on allergies, past medical history, family history, social history and a comprehensive review of systems which can be easily selected to indicate positive responses and, where appropriate, pertinent negative responses.

111. Nurse Notes Module—This series of screens allows nurses to easily select ordered procedures which have been performed, indicate other activities they have performed, record vitals, note observations or patient responses. Nurses can also pre-queue patient instructions associated with their activities. Orders made by physicians are queued so nurses can "pick off" an order to fully document the completion of the order. Electronic signatures can be added to a nurse's portion of the medical record.

112. Prephrased Text Module—Medical person specific or system wide blocks of text can be personalized. When selected, text blocks are automatically copied to the appropriate medical component of the medical record. They can then be easily modified in the transcript module, if necessary.

113. Transcript Module—Dictated text can be automatically integrated into the appropriate medical component of the record. Physicians can dictate parts of the medical record to a dictation company or in-house dictation department. The department can send the dictation back to TeleMed by modem or other link and TeleMed will automatically connect the dictation to the proper patient, separate the paragraphs and link them to the appropriate part of the patient's medical record. Once received, appropriate medical personnel can fully edit dictation text to fix errors or enhance the text with additional information.

Medical personnel can type text into the record if they choose, or use personalized prephrased text (text blocks previously entered by the physician) to enter preferred phraseology into the medical record.

114. Review of Systems Module—Review of systems is collected using a series of screens providing a comprehensive selection of medical facts on body systems. Extensive body subsystems are included. Responses can be easily selected to indicate positive responses, and where appropriate pertinent negative responses.

The module manages billing coding level alerts for review of system body systems used to warn medical personnel that this portion of the medical record is incomplete to support the level of billing possible based on accumulated facts about the visit. Indicators show what additional information should be collected. Coding alerts passed to master patient module for overall management.

The module also notifies the alerting system to warn medical personnel of significant medical conditions.

115. Drug Allergies Module—Drug allergies are tracked. The module notifies the alerting system to warn medical personnel of such allergies and where appropriate, drug interactions.

116. Lab Module—This section contains a comprehensive selection of lab tests and procedures to be ordered and tracked. A user can automatically generate orders within the appropriate hospital department and provide the ward clerk with a record of the order. Labels for laboratory test source materials are automatically printed. Lab results can be automatically deposited back into the TeleMed system. The return of results are automatically flagged on the active patient list screen to alert medical personnel.

Lab results which impact medical personnel actions, such as a result of pregnant, cause TeleMed to automatically begin alerting personnel to such conditions and future orders intelligently react to the condition. For example, an X-ray order would automatically indicate that the abdomen should be protected.

Results not received in a department specified time generate an alert.

All previous lab orders for a specific visit can be displayed to help prevent unnecessary duplication.

117. Radiology and Test Module—These section contains a comprehensive selection of radiology and test procedures to be ordered and tracked. A user can automatically generate orders within the appropriate hospital department and provide the ward clerk with a record of the order. Results can be automatically deposited back into the TeleMed system. The return of results is automatically flagged on the active patient list screen to alert medical personnel.

Results which impact medical personnel actions cause TeleMed to automatically begin alerting personnel to such conditions and future orders intelligently react to the condition.

Results not received in a department specified time generate an alert.

All previous radiology and test orders for a specific visit can be displayed to help prevent unnecessary duplication.

118. Diagnostics and Therapeutics Module—A comprehensive entry system for ordering or performing medical procedures. Procedures can be recorded upon completion or orders can be generated. If orders are made, a paper record of the order is created and the order is placed in queue for medical personnel to complete. The queuing system automates recording the completion of the order by personnel performing the task.

When procedures are performed, where appropriate, patient instructions are automatically queued.

119. ACLS Module—ACLS actions are recorded by selecting the procedure or observation and clicking record. Accumulated ACLS actions can be immediately displayed at any time with elapsed times since each action.

120. Laceration Module—TeleMed handles any number of lacerations per encounter and tracks activity performed overall, on each tissue layer, and on each laceration while pre-queuing appropriate patient instructions.

121. Inventory Control Module—This module controls the inventory and access for pharmaceutical and other materials used in the department. An automatic reordering system linked to other hospital systems is included.

122. Video System Module—The video instruction system is managed by this module. On demand, digital video instructions and education programs can be played for the patient through the terminal or an optional alternate screen. Video programming is also included to assist in obtaining informed consent for performing medical procedures.

123. Drug Module—Both a customizable physician-specific drug list and a comprehensive master drug list are available. The physician-specific list allows physicians to prescribe or order medications in their preferred manner, even allowing for the multiple entry of the same drug with different dosing. The master list can be accessed by entering the first few letters of the drug name or selection can be made by drug classification. Medications from the master list provide a default normal SIG for the drug, which can easily be modified. Drug interaction alerts are included.

Prescriptions include complete printed instructions in English or Spanish on use of the drug.

124. Consultation Module—Consultants can be selected from a directory. The directory displays all consultants or consultants filtered for medical specialty and/or managed care affiliations. A record of the consultation, along with timing and documentation of the discussion are recorded. If the consultant does not return a call within a department specified time period, an alert is generated.

125. Referrals Module—Referrals can be selected from the directory. The directory displays all consultants or consultants filtered for medical specialty and/or managed care affiliations. Referrals will print on the patient instructions along with specialty, phone numbers, addresses, and appointment times (if any).

126. Dr. Interval Module—The physician can record each time he/she checks the patient.

127. Medical Summary Module—This module specifies the range of facts, method of display, routing of output and other factors needed by the language generator.

128. Nurse Notes Summary Module—This module specifies the range of facts associated with nurse activity, method of display, routing of output and other factors needed by the language generator.

129. EKG Results Module—This module specifies the range of facts associated with EKG results, sets display to the screen, and establishes other factors needed by the language generator.

130. Patient Instructions Module—Integrated patient instructions are automatically queued based on the patient's condition and what was done. Instructions can be added or deleted from the queue before printing.

Printed instructions include a list of prescriptions, referrals and other significant information about the visit.

131. Work/School Excuse Module—Outputs patient work or school excuse noting services performed, when to return, limitations on activity, and referrals.

132. Demographics Module—This module tracks a comprehensive array of patient demographics including contact information, religion, insurance, employer, guarantor, etc. With insurance companies and government agencies that are equipped, automatic electronic insurance verification is made.

133. Department Clerk Module—Manages status of orders to other departments, and time delay alerts for non completion of orders.

134. Teleconferencing Module—From any point within the system (or from properly authorized remote locations) to any other point in the system, medical personnel can link terminals and have visual conferences. Medical personnel can link directly to a patient's room terminal and answer queries. Physicians can link from their office and have a conference with department personnel or the patient. Physicians in their office can remotely examine the electronic medical record and place orders or enter information into the medical record.

135. Research Module—This module can automatically strip identifying demographics from medical records and produce various analysis for generation of research data. Research protocols and outcome analysis can also be managed.

136. Transcript Text Analysis Module—TeleMed's communications server receives the text from the dictation source. This module analyzes the text for tags which identify the patient, dictating physician, time and date dictated and other data. Paragraphs are analyzed for tags indicating the medical record component associated with each paragraph. The dictation is then broken into paragraph based components, linked to the proper patient, date and timed stamped, and stored.

The module specifies the range of facts, method of display, routing of output and other factors needed by the language generator. The language generator is queued to automatically print medical records upon receipt of a transcript for any outstanding dictation if the patient is no longer in the department.

137. Automatic Backup Module—Provides automatic on-line back-up data. At department specified frequency, the module also backs-up all data changed since the last full back-up (interim backups).

138. Scheduling Module—This module manages scheduling of personnel for department coverages.

139. Interface Module—Interface, and data mapping to exchange data with other systems is managed by this module.

TeleMed is a comprehensive system for the automatic generation of a medical English sentence structured medical record as a consequence of individual factual data entry. The look and feel of the program is designed to make the program easy to use by medical personnel having little or no computer experience and to dramatically shorten the learning curve to become competent in using the system.

TeleMed stations with touch screens are placed at each bedside, nurse and physician stations, triage, clerk desks and other appropriate locations.

Use of the system is accomplished by using either the touch screen, keyboard or mouse and selecting a screen button or box to move through the program or enter medical facts. Values can be entered by keyboard. The system intelligently selects appropriate variations of screens to fit the patient (such as appropriate sex).

Personnel using the system must clearly demonstrate their identity using a variety of methods depending on the system configuration. Single and multiple passwords, smart card, magnetic card or other personal ID technologies. The user's identity establishes the individual "rights" to use various functions. For example, physicians may be the only users given rights to generate prescriptions, nurses could have rights to implement various medical procedures, ward clerks might need rights to order labs, but records clerks may be limited to changing demographic information. If smart cards are used, the system is available only while a proper, authorized card is inserted. Upon withdrawal, the system completes any processes and reverts to a non responding mode Remote access to the system is controlled by "firewall" software routines which require varying security levels up to a forced return link initiated by the system to authorized remote computers or systems.

Medical personnel need to quickly see the status of both individual patients and the entire department. TeleMed initially displays an active patient list showing all patients within the department. This display also provides a variety of additional pertinent information such as location, priority, elapsed time since entering the department, order status, vitals status and assigned physician.

This information can be presented in a variety of formats, sometimes with additional information, to help the medical personnel quickly obtain the patient tracking information they need. Department layout displays a map of the department showing occupancy (and availability) and physician assignments. Waiting patients shows patients in the order they should be taken. Patient complaints presents patients with their associated complaints. A patient can be selected from any of these displays to enter his/her individual medical record.

Other displays show outstanding orders and the latest vitals on each patient.

Historical medical records can be located using a variety of patient information such as name, social security number or previous hospital numbers. Using a name will display all patients with similar names with additional identifying characteristics such as birth date. The specific patient can be selected and previous visits will be displayed with complaints. Selection of a visit provides access to a medical record summary for that visit.

Movement of a patient is noted by a simple selection of available locations (occupied beds are excluded from the selection).

TeleMed tracks a comprehensive array of patient demographics including contact information, religion, insurance, employer, guarantor, etc.

The triage portion of the program allows personnel to begin entering patient facts before knowing the patient identification. This section collects specifics about the medical encounter that are later intelligently used by the system. Facts such as pregnancy status later cause the system to automatically alert medical personnel as procedures are about to be performed, and warn personnel when orders are given (such as specifying abdominal protection when x-rays are ordered). Upon completion of triage, a triage summary produced by the language generator can be printed.

TeleMed is a complaint driven system. As complaints are entered, the system begins to automatically modify later functions so personnel deal with a dramatically reduced array of selections. For example, a comprehensive differential diagnosis is filtered to only those appropriate to the patient's complaint, sex and age, and a recommended multilevel subset (none, light, medium or heavy) is used as a starting point for physicians to place in the medical record. They can then easily add to or delete from this starting point. Patient instructions relating to a complaint/diagnosis are automatically queued.

When a complaint is selected, an extensive knowledgebase is used by the program to establish parameters the program will follow throughout the rest of the visit. These parameters guide the program in selection of screens (such as to address the appropriate sex), generation of text, billing code levels, order restrictions or enhancements, etc. As the encounter progresses, the parameters are modified by the program to fit new facts collected.

The final diagnosis(es) can be easily selected from (but is not limited to) the differential diagnosis. Trauma diagnosis(es) can be selected from graphic presentations of the appropriate body parts. For example, a particular fractured bone and the fracture location, characteristics, and type can be indicated on a graphical display of the body part. TeleMed converts the fracture facts into proper medical English describing the injury.

A series of screens provides a comprehensive selection of medical facts on allergies, past medical history, family history, social history and a comprehensive review of systems which can be easily selected to indicate positive responses, and where appropriate pertinent negative responses.

The nurse notes series of screens allows nurses to easily select ordered procedures which have been performed, indicate other activities they have performed, record vitals, note observations or patient responses. Nurses can also pre-queue patient instructions associated with their activities. Orders made by physicians are queued so nurses can "pick off" the order to fully document the completion of the order.

The ordering section contains a comprehensive selection of labs, radiology procedures and other tests to be ordered and tracked. A user can automatically generate orders within the appropriate hospital department and provide the ward clerk with a record of the order. Results from these departments can be automatically deposited back into the TeleMed system. The return of results is automatically flagged on the active patient list screen to alert medical personnel.

Lab results which impact medical personnel actions, such as a result of pregnant, cause TeleMed to automatically begin alerting personnel to such conditions and future orders intelligently react to the condition. For example, an X-ray order would automatically indicate that the abdomen should be protected.

All previous lab, radiology or test orders for a specific visit are displayed to help prevent unnecessary duplication.

The procedures section is a comprehensive entry system for ordering or performing medical procedures. Procedures can be recorded upon completion or orders can be generated. If orders are made, a paper record of the order is created and the order is placed in queue for medical personnel to complete. The queuing system automates recording the completion of the order by personnel performing the task.

When procedures are performed, where appropriate, patient instructions are automatically queued.

Advanced cardiac life support (ACLS) actions are recorded by selecting the procedure and clicking on record. Accumulated ACLS actions can be immediately displayed at any time with elapsed times since each action.

TeleMed handles any number of lacerations per encounter and tracks activity performed overall, on each tissue layer, and on each laceration while pre-queuing appropriate patient instructions.

Both a customizable physician-specific drug list and comprehensive master drug list are available. The physician-specific list allows physicians to prescribe or order medications in their preferred manner, even allowing for the multiple entry of the same drug with different dosing. The master list can be accessed by entering the first few letters of the drug name or by drug classification. Medications from the master list provide a default normal SIG for the drug, which can easily be modified.

Generated prescriptions include complete printed instructions in English or Spanish on use of the drug.

Consultants can be selected from a directory. The directory displays all consultants or consultants filtered for medical specialty and/or managed care affiliations. A record of the consultation, along with timing and documentation of the discussion are recorded.

Referrals can be selected from the same directory. Referrals will print on the patient instructions along with specialty, phone numbers, addresses, and appointment times (if any).

TeleMed automatically integrates dictated text into the appropriate part of the medical record. Physicians can dictate parts of the medical record to a dictation company or in-house dictation department. The department can send the dictation back to TeleMed by modem or other link and TeleMed will automatically connect the dictation to the proper patient, separate the paragraphs and link them to the appropriate component of the patient's medical record.

TeleMed's communications server(s) receives the text from the dictation source. The text is analyzed to identify the patient, dictating physician, time and date dictated and other data. Paragraphs are analyzed for tags indicating the medical record component associated with each paragraph. The dictation is then broken into paragraph based components, linked to the proper patient, date and timed stamped, and stored.

Once received, appropriate medical personnel can fully edit dictation text to fix errors or enhance the text with additional information.

Physicians can type text into the record if they choose, or use personalized prephrased text (text blocks previously entered by the physician) to enter preferred phraseology into the medical record.

The physician can record each time he/she checks on the patient.

Integrated patient instructions are automatically queued based on the patient's condition and what was done. Instructions can be added or deleted from the queue before printing.

Printed instructions included a list of prescriptions, referrals and other significant information about the visit.

A key function within the TeleMed program is the language generator. TeleMed stores most medical information as individual specific medical facts rather than as text. When displaying these facts in an on-screen medical summary or printed medical record, these facts are quickly converted to complex sentence structure similar to a physician's dictated text.

The TeleMed language generator builds sentence structure, often containing multiple related facts taken from widely separated points within the program. The program uses a pronoun sequencing technique which produces medical sentences sounding more like the way medical people actually record medical records.

Medical facts are analyzed for responses and type, reordered and converted to initial sentence structure. Text such as dictation is analyzed for type and integrated into the previous structure. The text is then analyzed for the need for headlines and subheads. Needed heads are inserted. The entire block is analyzed and reformatted to combine and rebreak text lines at appropriate points. The block is reanalyzed and reformatted for positioning on the appropriate output (screen or print).

Medical records are printed in a typeset format whereby all medical facts are grouped under the proper medical headings. Where appropriate, TeleMed intelligently rearranges the order in which facts are entered to provide the information in an extremely usable format. The use of bold increased-size headings for major sections and bold or italic subheads allow for quick viewing and easy location of specific facts.

The medical record is automatically printed upon receipt of any outstanding dictation if the patient is no longer in the department.

TeleMed can automatically fax a copy of the patient's record to the patient's private physician.

The program can also automatically generate an extra copy of medical records for patients with specific diagnosis or other characteristics for audit.

Coding level alerts are used to warn medical personnel that the medical record in incomplete to support the level of billing possible based on accumulated facts about the visit. Indicators show what additional information should be collected.

An extensive selection of physician and management reports are available. Since TeleMed stores medical facts as discrete facts rather than text, extensive analysis of an extremely wide variety of medical relationships can easily be accomplished.

A variety of maintenance utility functions are included.

A set of wound treatment screens provides a method for documenting multiple layers of repair using different suture techniques on different tissue layers with different suture material.

Each time a doctor visits a patient can be recorded, along with date/time data, by TeleMed.

A graphical representation of all bones in the body can be displayed so specific bones, location on the bone, type of fracture, and other fracture related facts can be indicated. The peripheral CPU stores the fact data and also generates a medical English description of the fracture for review. The CPU sends the data and text to the file servers for storage as diagnoses. Patient instructions associated with fracture repair procedures are automatically queued by TeleMed.

The review of systems uses a series of screens on the peripheral CPU's whereby entries are made by touching or clicking a mouse on the check boxes, thereby recording data about certain specific organ systems in question. That data is then transferred as data to the file servers and is stored as data.

The coding level alerts are a method by which the software on the peripheral CPU generates check marks next to the screen data entry buttons, which notify the treating nurse to go into those screens and enter that specific data. The check marks are generated by the entry of specific complaints made by a patient. Specific check marks are converted into diamonds when sufficient medical data has been collected to meet coding level requirements for that medical component or function in association with accumulated single or multiple complaint requirements.

Pregnancy linking is a methodology by which, if the patient is stated to be or determined to be pregnant, or possibly pregnant, TeleMed automatically alerts medical personnel to take precautions when procedures, such as X-rays are to be performed. TeleMed also automatically calculates the estimated date of completion and gestational age.

Upon completion of the medical encounter, or at any time during the encounter, TeleMed can generate a complete medical English summary of all accumulated information about the encounter. If dictation has been made, TeleMed will automatically process the transcription text into the patients medical record for that specific visit and generate a printed summary.

An example of a complete generated patient report, lab and radiology requests, patient instructions and prescription follows.

EXAMPLE

Southwest General Hospital

San Antonio, Texas                                    Emergency Department Report

| Patient Name<br>Garbo, Greta G | | Sex<br>Female | DOB<br>09/21/58 | Age<br>37 year old |
|---|---|---|---|---|
| Arrival Date/Time<br>03/28/96   11:18 | Admission #<br>6478636 | Patient #<br>788231 | Last Tetanus<br>5-10 Years | Status<br>Urgent |

General Information
The informant is the patient and EMS.

Chief Complaint
The patient's first complaint is falling.
The patient's second complaint is injury, left wrist.
The patient's third complaint is hematuria.
The patient's fourth complaint is abrasion, right knee.

History of Present Illness
Onset of the problem occurred at approximately 10:53 on 03/28/96.
This patient was walking across the street when she fell and hurt her left wrist and right knee. She also bumped her lower abdomen on the curb. She subsequently noted blood in the toilet when she urinated and is not on her period. She missed the last one and thinks she's probably pregnant again because she's urinating frequently and has had some morning sickness. She denies any head or neck trauma and does not feel faint. No cold sweats or SOB.

Allergies
Demerol, sulfa.

Medications
Current medications: None.

Past Medical History
Patient's physician: None. Her last tetanus shot was between 5-10 years ago. Tetanus is not up to date. Past medical history includes: anemia, back injury and pneumonia.

Past Surgical History
Past surgical history includes: appendectomy and C-section.

Review of Systems
She is complaining of coughing. The skin has no rash. There has been no bruising. Mrs. Garbo complained of: no musculoskeletal pain and no joint or muscle stiffness. HEAD: no history of headaches, no previous head trauma and no history of syncope. EYES: no vision problems, no photophobia and no previous discharge from the eye. EARS: no deafness or hearing loss and no previous ear pain. NOSE: (+) rhinitis and no sinusitis. MOUTH: no mouth ulcers. THROAT: no sore throat and no previous dysphagia. NECK: no prior stiffness and no neck pain. PULMONARY: no pleuritic pain, no shortness of breath, no dyspnea while sleeping, (+) for cough, no sputum production and no hemoptysis. CARDIAC: no chest pain, no palpitations and no orthopnea. GASTROINTESTINAL: (+) for nausea. The patient denies vomiting, abdominal pain, diarrhea, constipation, hematemesis, melena and bloody stools. GENITOURINARY: The patient is pregnant. recent onset of polyuria, recent onset of nocturia, mild dysuria, urgency, increased frequency of urination, hematuria with no clots and vaginal discharge. The patient denies incontinence and dyspareunia. Venereal: She has not been treated for venereal disease. Onset of menses was at age 11. Periods occur regularly approximately every 30 days and usually last for 4 days with medium flow. The date of the last normal period was 01/12/96. The next to last period occurred four weeks prior to the last period. Complications of pregnancy included: fluid retention and

Patient Record

Southwest General Hospital

San Antonio, Texas

Emergency Department Report

| Patient Name<br>Garbo, Greta G | | Sex<br>Female | DOB<br>09/21/58 | Age<br>37 year old |
|---|---|---|---|---|
| Arrival Date/Time<br>03/28/96 11:18 | Admission #<br>6478636 | Patient #<br>788231 | Last Tetanus<br>5-10 Years | Status<br>Urgent | a C-section.

Social History
The patient is a cigarette smoker using 1/2 PPD. Alcohol use includes wine weekly. She denies use of drugs. Mrs. Garbo is married. The patient lives with a spouse and children.

Family History
There is a family history of blood relatives with cancer, diabetes, heart disease, high blood pressure and stroke.

Physical Exam
Initial vital signs: T 97.8 (O), P 95, R 24, BP 112/68, O2 Sat 97%, Wt 54 kg (118 lbs). She is a 37 year old caucasian pregnant female. The calculated EDC is 10/18/96 based on the patient's stated LMP. The calculated gestation is 11 weeks. Mrs. Garbo has a height of 5' 3" and weighs 54 kg. (118 lbs.) (weighed)

MUSCULOSKELETAL: The left wrist is somewhat swollen and is very tender to palpation and she has pain on range of motion. There is no gross angular deformity. The right knee has superficial abrasions and a little bit of dirt ground in. There is slight pain in the knee on ROM but no instability or crepitus or restriction of ROM.

ABDOMEN: is soft with slight tenderness over the symphasis but there is no swelling or bladder distention. Flanks are non-tender.
GENERAL APPEARANCE: Well hydrated, well nourished, cooperative patient. No acute distress.
MENTAL STATUS: Oriented X 3, normal affect, behavior, insight, judgement, mood, perception, and thought process.
HEAD: No sinus tenderness. No facial tenderness or swelling. No tenderness of the scalp and no scalp hematomas. No palpable nodes. No apparent head trauma and no skull deformity or depression.
MOUTH: Mucous membranes: moist. Tongue: normal. Gums: normal. No patches or ulcers. Uvula midline.
DENTAL: no local swelling, redness or tenderness. Normal dentition. Good hygiene.
NECK: supple, no tenderness, no spasm, range of motion within normal limits. No lymphadenopathy. No rigidity. Negative Kernig's and Brudzinski's signs. No JVD. No carotid bruits. Equal bilateral carotid pulses. No palpable enlargement of the thyroid and no thyroid masses or tenderness. Normal glottic motion on swallowing. No trachael deviation.
CHEST: there are no retractions. There is no tenderness on palpation of the chest wall. Chest is symmetrical. There is no crepitus.
HEART: Rate: normal. Rhythm: regular. Heart Sounds: normal. No systolic or diastolic murmurs. No pericardial rub. No gallops. There is no ectopy. No displacement of the PMI.
LUNGS: breath sounds equal bilaterally. No dullness to percussion. No rhonchi, rubs, wheezes, or rales on auscultation. Not hyperresonant. No E to A changes.
BACK: no tenderness, without spasm. There is no observed scoliosis of the spine. There is no point tenderness. Bilateral straight leg raising negative. There is no CVA tenderness or pain on palpation.
GENITOURINARY: Vulva: no ulcers, no vescicles, and no atrophy. No lice found. Vagina: normal introitus, no discharge or blood. Cervix: closed, (+) Chadwick's sign, nontender,

Patient Record

C286478636 Printed 03/28/96 13:33 Page 2 Continued
= ©RLIS, Inc. TeleMed

Southwest General Hospital
San Antonio, Texas

Emergency Department Report

| Patient Name<br>Garbo, Greta G | | Sex<br>Female | DOB<br>09/21/58 | Age<br>37 year old |
|---|---|---|---|---|
| Arrival Date/Time<br>03/28/96  11:18 | Admission #<br>6478636 | Patient #<br>788231 | Last Tetanus<br>5-10 Years | Status<br>Urgent | non-specific discharge, no cystic changes present. Uterus: slightly enlarged, nontender. Right Side Adnexae: without mass, nontender. Left Side Adnexae: full left ovary, slightly tender to palpation. No fullness in the cul-de-sac.

RECTAL: nonbloody stool. No hemorrhoids are noted. No inguinal hernia is present. No impaction.

NEUROLOGICAL: alert, oriented to time, place and person. Cranial Nerves: II-XII normal. Motor Function: normal tone and strength. Sensory Function: normal to pain and soft touch. Cerebellar Function: normal giat and rapid alternating movements. Reflexes: normal in intensity and symmetric.

Labs

03/28/96 11:31 labs requested by William L. Phillips, RN
Labs requested include: CBC, serum pregnancy (HCG), urinalysis, urine C&S and ER panel.
Lab results of 11:42:19:

Hematology

| | |
|---|---|
| CBC WBC | 4.9 K/UL (4.8-10.8) |
| CBC RBC | 3.9 M/UL (4.2-5.8) |
| CBC Hgb | 11.1 G/DL (12-16) |
| CBC Hct | 32.9 % (38-48) |
| CBC MCV | 79 FL (81-99) |
| CBC MCH | 26 PG (27-31) |
| CBC MCHC | 31 G/DL (33-37) |
| CBC Plt Count | 228 K/UL (140-400) |
| Differential Segs | 62 % (36-63) |
| Differential Bands | 2 % (0-9) |
| Differential Lymphs | 32 % (20-45) |
| Differential Monos | 3 % (3-11) |
| Differential Eosin | 1 % (0-6) |
| Morphology Micro | Positive |
| Morphology Hypochromasia | Positive |
| Morphology Oval | Positive |

Urinalysis

| | |
|---|---|
| Color | Red (Normal is Amber) |
| Appearance | Hazy (Normal is Clear) |
| Specific Gravity | 1.024 (1.00-1.035) |
| pH | 7.5 (4.6-8.0) |
| Protein | 1+ (Negative) |
| Glucose | Negative (Normal) |
| Ketones | 1+ (Negative) |
| Bilirubin | Negative (Normal) |
| Occult Blood | 2+ (Negative) |
| Leuko Esterase | 1+ (Negative) |
| Nitrite | Negative |
| Urobilinogen | Negative (Normal) |
| Protein Confirmation by Sulfosalicilic Acid | 1+ (Negative) |

Patient Record

Southwest General Hospital

San Antonio, Texas

Emergency Department Report

| Patient Name<br>Garbo, Greta G | | Sex<br>Female | DOB<br>09/21/58 | Age<br>37 year old |
|---|---|---|---|---|
| Arrival Date/Time<br>03/28/96  11:18 | Admission #<br>6478636 | Patient #<br>788231 | Last Tetanus<br>5-10 Years | Status<br>Urgent |

Lab results of 11:44:41:

*Chemistry*

| | |
|---|---|
| NA | 139 Meq/L (136-149) |
| K | 3.2 Meq/L (3.5-5.0) |
| CL | 102 Meq/L (99-110) |
| CO2 | 26 Meq/L (24-31) |
| BUN | 12 Mg/L (10-26) |
| Creatinine | 0.8 Mg/L (0.6-1.5) |
| Glucose | 118 Mg/L (70-110) |
| Alk Phos | 103 MU/ML (Adult 30-100, Child 3-4 X Adult |
| SGOT | 28 IU/L (0-40) |
| SGPT | 31 IU/L (0-40) |
| LDH | 153 IU/L (90-180) |
| T Bili | 1.0 Mg/DL (0.2-1.5) |
| CA | 10.1 Mg/DL (8.5-10.5) |
| CA++ | 4.3 Mg/DL (4.0-4.8) |
| Mg | 2.1 Mg/DL (1.8-2.6) |
| Protein | 6.8 Mg/DL (6-8) |
| Chol | 126 Mg/DL (50-199) |
| Amylase | 26 Mg/DL (25-115) |

*Special Chemistry*

| | |
|---|---|
| Serum Pregnancy | Positive |
| Serum Lipase | 19 U/L (7-60) |

X-Rays

03/28/96 11:32 Radiology requested by William L. Phillips, RN
X-ray requests include: left wrist and right knee.

03/28/96 12:10 Radiology requested by James Ross, Jr., MD
Ultrasound request: pelvis.

Left wrist: non-displaced impacted distal radius fracture. No ulna styloid fracture. Normal scaphoid and other carpals without fracture or subluxation. Right knee: no fractures or subluxation, no joint effusion, no calcified Baker's cyst, no degenerative changes or joint narrowing.
Pelvic Ultrasound: the ultrasound confirms a 10 week, 3 day, viable intrauterine pregnancy. There is a corpus luteum cyst on the left. There is no free fluid in the cul-de-sac. No appendix is visualized.

Procedures & Therapeutics

03/28/96 11:36
The wound was treated with Neosporin and Adaptic and plain gauze dressing. For splinting a volar forearm splint was applied.

03/28/96 12:36
Administered Ampicillin Sodium 1 GM, Ampicillin Sodium For Inj 1 GM: 1 gm IV now.

Patient Record

Southwest General Hospital

San Antonio, Texas                                             Emergency Department Report

| Patient Name<br>Garbo, Greta G | | Sex<br>Female | DOB<br>09/21/58 | Age<br>37 year old |
|---|---|---|---|---|
| Arrival Date/Time<br>03/28/96  11:18 | Admission #<br>6478636 | Patient #<br>788231 | Last Tetanus<br>5-10 Years | Status<br>Urgent |

03/28/96 12:40
Administered Diphteria and Tetanus Toxoids, Tetanus-Diphtheria Toxoids (Td) Inj 5-1.5
LFU: 0.5 cc IM Administered now.

03/28/96 13:17
Orders were given to release the patient.

03/28/96 13:22

Emergency Department Course

Differential Diagnosis
The differential diagnosis for the third complaint, hematuria, includes: uncertain etiology; acute cystitis; ureteral calculus; neoplasm; coagulopathy; acute appendicitis; acute diverticulitis; acute pyelonephritis; renal cyst; renal neoplasm; and glomerulonephritis.

Consultations
Frank Garcia specializing in Orthopedics was consulted on 03/28/96 at 13:16. The case was discussed at length. Consultant wishes to see the patient.

Bebe T Newbirth specializing in OB-GYN was consulted on 03/28/96 at 13:35. The case was discussed, consultant concurs with the decision to discharge patient. Consultant wishes to see the patient in her office tomorrow.

Diagnosis
1: fall.
2: impacted fracture of the left distal radius.
3: acute cystitis with hematuria.
4: abrasion, right knee.

Referrals
The patient was referred to:
   Bebe T Newbirth, OB-GYN
   Frank Garcia, Orthopedics

Prescriptions
Prescriptions given to the patient include:
TYLENOL #3 Tab 300-30MG, quantity 12, 1-2 tablets every 4 to 6 hours as needed, for 3 days.
MACROBID CAP100MG, quantity 14, 1 cap po q 12°, for 7 days.

Work/School Limitations/Excuse
A work excuse was provided to the patient. The excuse itemized services performed to include: initial treatment, radiology, lab work, physical exam, splint application. The patient may return to modified work on 04/02/96. She should not do any prolonged standing or walking. Mrs. Garbo should participate in right handed work only. Mrs. Garbo should not work near moving machinery. The patient should limit lifting to no more than 10 lbs.

Patient Record

Southwest General Hospital

San Antonio, Texas                                               Emergency Department Report

| Patient Name<br>Garbo, Greta G | | Sex<br>Female | DOB<br>09/21/58 | Age<br>37 year old |
|---|---|---|---|---|
| Arrival Date/Time<br>03/28/96  11:18 | Admission #<br>6478636 | Patient #<br>788231 | Last Tetanus<br>5-10 Years | Status<br>Urgent |

Release from Emergency Department
She was released in good condition. Mrs. Garbo was released from the hospital on 03/28/96 at 13:18.

---

James Ross, Jr., MD

C286478636  Printed 03/28/96 13:34 Page 6
= ©RLIS, Inc. TeleMed

Patient Record

Southwest General Hospital

San Antonio, Texas                                                    Emergency Department Report

| Garbo, Greta G | | Female | 09/21/58 | 37 year old |
|---|---|---|---|---|
| Arrival Date/Time<br>03/28/96  11:18 | Admission #<br>6478636 | Patient #<br>788231 | Last Tetanus<br>5-10 Years | Status<br>Urgent |

Nursing

*Vitals*

| Date | Time | Pulse | Resp | BP | Temp | O2Sat | BGlu | FHrt | Recorded By |
|---|---|---|---|---|---|---|---|---|---|
| 03/28/96 | 11:27 | 95 | 24 | 112/68 | 97.8 (O) | 97% | | | William L. Phillips, RN |
| 03/28/96 | 11:33 | 89 | 24 | 110/65 | 98.4 (O) | | | | Jimmie McBride, RN |

*Orthostatic Vitals*

| Date | Time | P BP Rec | P BP Sit | P BP St | Recorded By |
|---|---|---|---|---|---|
| 03/28/96 | 11:33 | 87  110/64 | 85  109/71 | 96  114/78 | Jimmie McBride, RN |

*Nurse Assessment*
The patient is assessed in triage as urgent.
Assessment recorded by William L. Phillips, RN
Treatment prior to arrival included sling, wound dressing.

Patient states that she was crossing the street and tripped on the curb. She fell onto her outstretched left hand and injured the left wrist and abraded her right knee. However she went home and on going to the bathroom she noted bloody urine in the toilet. She is not on her period. She missed her last period and wonders if she might be pregnant. The patient is awake, alert, attentive, moving all extremities well. The patient indicates a normal appetite. Skin W/D, pink nail beds, less than 2 second capillary refill. No obvious deformity. No respiratory distress. No neurovascular deficit to the injured area. No nausea, vomiting or diarrhea.

*Nurse Notes*
03/28/96 11:33 Nurse note recorded by Jimmie McBride, RN

She is oriented to time, place and person. Speech is normal. The left arm has normal strength. The right arm has normal strength. The left leg has normal strength. The right leg has normal strength. The left arm, right arm, left leg and right leg have normal pinprick sensation. Mrs. Garbo has a tachycardia. Breathing is normal. Breath sounds are clear. The skin is moist. The skin feels cool. The skin color is pale. Capillary return is normal. The pupils are equal. Both pupils are normally reactive. Both left and right radial pulses are normal. Both left and right tibial pulses are normal. The abdomen is tender in the left lower quadrant and right lower quadrant. The abdomen is distended. Bowel sounds are normal.

03/28/96 11:39 Nurse note recorded by Allison Reed, RN
The patient has been moved to x-ray.

03/28/96 11:45 Nurse note recorded by Jimmie McBride, RN

Physician orders completed include: Apply a volar forearm splint. Apply Neosporin ointment to the wound. Dress the wound using Adaptic and plain gauze dressing. She complains of increasing left wrist pain. Mrs. Garbo feels weak.

03/28/96 12:25 Nurse note recorded by Jimmie McBride, RN
The patient has been moved to ultrasound.

Patient Record

Southwest General Hospital

San Antonio, Texas                                     Emergency Department Report

| Patient Name<br>Garbo, Greta G | | Sex<br>Female | DOB<br>09/21/58 | Age<br>37 year old |
|---|---|---|---|---|
| Arrival Date/Time<br>03/28/96  11:18 | Admission #<br>6478636 | Patient #<br>788231 | Last Tetanus<br>5-10 Years | Status<br>Urgent |

03/28/96 12:51 Nurse note recorded by Jimmie McBride, RN
She has returned to the emergency department.

03/28/96 12:59 Nurse note recorded by Jimmie McBride, RN

Physician orders completed include: Diphteria and Tetanus Toxoids, Tetanus-Diphtheria Toxoids (Td) Inj 5-1.5 LFU: 0.5 cc IM now.

03/28/96 13:18 Nurse note recorded by Jimmie McBride, RN

Physician orders completed include: Discharge the patient.
Mrs. Garbo was ambulatory upon leaving the Emergency Department. The patient was escorted from the Emergency Department by family. She appears to have complete or near complete relief of symptoms. Mrs. Garbo is alert and oriented. There are no other complications. Instructions were given to the appropriate person. The responsible party voiced understanding of the instructions. The patient was provided with a copy of the lab report and prescriptions.

William L. Phillips, RN

Jimmie McBride, RN

Allison Reed, RN

Patient Record

Southwest General Hospital

San Antonio, Texas  
Emergency Department

03/28/96  
12:11

Requested Labs

| Admission # 6478636 | Patient # 788231 | Room/Bed Unknown |
|---|---|---|
| Patient Garbo, Greta G | | 37 Year Old |
| Doctor James Ross, Jr., MD | | Order entered by James Ross, Jr., MD |

| | |
|---|---|
| 1 | CBC |
| 2 | Serum Pregnancy (HCG) |
| 3 | Urinalysis |
| 4 | Urine C&S |
| 5 | ER Panel |

*Lab Copy*

©RLIS TeleMed

Southwest General Hospital

San Antonio, Texas
Emergency Department

03/28/96
12:12

Requested Radiology Procedures

| Admission # 6478636 | Patient # 788231 | Room/Bed Unknown |
|---|---|---|
| Patient Garbo, Greta G | | 37 Year Old Pregnant Female |
| Doctor James Ross, Jr., MD | | Order entered by James Ross, Jr., MD |

SHIELD ABDOMEN
Knee with Sunright Right
Wrist Left
Pelvic Ultrasound

*Radiology Copy*

©RLIS TeleMed

Southwest General Hospital

San Antonio, Texas  Emergency Department Report

| Patient Name<br>Garbo, Greta G | | Sex<br>Female | DOB<br>09/21/58 | Age<br>37 year old |
|---|---|---|---|---|
| Arrival Date/Time<br>03/28/96  11:18 | Admission #<br>6478636 | Patient #<br>788231 | Last Tetanus<br>5-10 Years | Status<br>Urgent |

Initial Vital Signs
T 97.8 (O), P 95, R 24, BP 112/68, O2 Sat 97%, Wt 54 kg (118 lbs).

General Information
The informant is the patient and EMS. The patient is to be seen by the emergency department physician.

Chief Complaint
The patient's complaint is falling.
The patient's second complaint is injury, left wrist.
The patient's third complaint is hematuria.
The patient's fourth complaint is abrasion, right knee.

Allergies
Demerol, sulfa.

Medications
Current medications: None.

Past Medical History
Patient's physician: None. Her last tetanus shot was between 5-10 years ago. Tetanus is not up to date. Past medical history includes: anemia, back injury and pneumonia. The date of the last normal period was 01/12/96.

Past Surgical History
Past surgical history includes: appendectomy and C-section.

Nursing Triage Assessment
Assessment recorded by William L. Phillips, RN
The patient arrived for triage at 03/28/96 11:18.
The patient is assessed in triage as urgent.
She is a 37 year old caucasian pregnant female. The calculated EDC is 10/18/96 based on the patient's stated LMP. The calculated gestation is 11 weeks. Mrs. Garbo has a height of 5' 3" and weighs 54 kg. (118 lbs.) (weighed) Onset of the problem occurred at approximately 10:53 on 03/28/96. Treatment prior to arrival included sling, wound dressing.

Patient states that she was crossing the street and tripped on the curb. She fell onto her outstretched left hand and injured the left wrist and abraded her right knee. However she went home and on going to the bathroom she noted bloody urine in the toilet. She is not on her period. She missed her last period and wonders if she might be pregnant. The patient is awake, alert, attentive, moving all extremities well. The patient indicates a normal appetite. Skin W/D, pink nail beds, less than 2 second capillary refill. No obvious deformity. No respiratory distress. No neurovascular deficit to the injured area. No nausea, vomiting or diarrhea.

William L. Phillips, RN

Triage Record

Southwest General Hospital

San Antonio, Texas  
Emergency Department

03/28/96  
12:13

Report of Treatment

Garbo, Greta G                                              Employed By

| | |
|---|---|
| Admission Number | 6478636 |
| Treated by | James Ross, Jr., MD |
| Date of Injury | 03/28/96 |
| Date of Treatment | 03/28/96 |
| Time of Treatment | 11:18 |

Status

Services performed included: initial treatment, radiology, lab work, physical exam, splint application.
The patient may return to modified work on 04/02/96.
The patient should not do any prolonged standing or walking. The patient should participate in right handed wor only. The patient should not work near moving machinery. The patient should limit lifting to no more than 10 lt

Referrals

Bebe T Newbirth  
  OB-GYN  
  Babies "R" Us  
  1654 Lullabye Lane  
  Suite #344  
  San Antonio, TX 78202  
  (210) 555-1222

Frank Garcia  
  Orthopedics  
  Ortho S.M.A.R.T.  
  7355 Barlite Blvd. #201

San Antonio, TX. 78224  
  222-2212

If you are unable to get a prompt appointment with the referral physician, call the Emergency Department for an alternate referral. If you any questions contact the Emergency Department.

Authorization is hereby granted to release the above information to my employer.
I also agree to and understand the recommended follow-up instructions.

Patient Signature                                                    Signature – James Ross, Jr., MD  
Employer Copy

Southwest General Hospital

San Antonio, Texas  
Emergency Department

03/28/96  
12:14

Patient Instructions

| Admission # 6478636 | Patient # 788231 | Room/Bed Unknown |
|---|---|---|

Patient Garbo, Greta G

You were Seen by Dr. James Ross, Jr., MD

The following instructions are important for your continued care.

ANTIBIOTIC THERAPY
You have been given an antibiotic prescription. It's important that you take all the medication, unless instructed otherwise by your physician. Failure to complete the entire course can result in relapse of your condition.

Common side effects of antibiotics include nausea, intestinal cramping, or diarrhea. Women may develop vaginal yeast infections, and babies can get yeast (thrush) in the mouth following the use of antibiotics. Contact your physician if you develop significant side effects from this medication.

Allergy to this antibiotic can result in hives, wheezing, faintness, or itching. If symptoms of allergy occur, stop the medication and call the doctor.

FRACTURED RADIUS
The bone called the radius is fractured. This type of fracture is typically caused by falling onto the outstretched hand. The fracture is not serious, however, and should heal well shows the bone is in good position to heal.

A cast or splint is used to protect the fracture. For the first few days after the injury, the arm should be elevated and ice packed. Healing takes from three to eight weeks, depending on the age of the patient and the seriousness of the fracture.

Your doctor has explained the treatment plan. It's important that you follow up as instructed to prevent complications. Call the doctor or return at once if severe pain or swelling occur, or if the hand becomes numb, swollen, or discolored.

SLING TO BE USED
You are to use a sling. This is to rest the area, and to prevent it from hanging downward. Use this sling for at least 48 hours (or longer if so instructed by the doctor). Some types of splints will break if not supported by the sling, so the sling must be used as long as the splint.

Ice can be placed inside the sling over the injured area.

Once you remove the sling, you should not encounter pain when you use the arm and hand. If you do feel pain beneath the cast or splint, you must continue use of the sling.

SPLINT PENDING CASTING
Your injury can't be casted until the swelling has subsided. Therefore a temporary splint has been placed to protect the injury.

Full use of an injured area is not possible in a splint. You should follow the doctor's instructions concerning rest, ice, and elevation of the injury. Never do anything which causes pain under the splint.

Keep the splint on ALL THE TIME until you return for casting. If there is unexpected severe pain, or numbness, discoloration, or swelling beyond the splint, you should return at once.

URINARY TRACT INFECTION
Your evaluation indicates that you have a urinary tract infection. This is due to germs growing in the bladder. This is a common problem.

This infection usually responds quickly to antibiotics. Your antibiotic should be taken exactly as prescribed. Drink plenty of fluids — 3 to 4 quarts a day.

Occasionally a bladder anesthetic will be prescribed to help stop the feeling of urgency until the antibiotic has a chance to clear the infection. This may cause your urine to be dark orange.

Certain urine infections require a culture. If the doctor obtained a culture, the results will be back in two days. You should call to see if a change in treatment is needed.

*Hospital Copy*   *Received By* _____   ©RLIS TeleMed

Southwest General Hospital

San Antonio, Texas  
Emergency Department

03/28/96  
12:14

Patient Instructions

| Admission # 6478636 | Patient # 788231 | Room/Bed Unknown |
|---|---|---|

Patient Garbo, Greta G

You were Seen by Dr. James Ross, Jr., MD

The following instructions are important for your continued care.

A repeat urinalysis after you finish treatment is often recommended. The physician will let you know if further testing is required.

Call the doctor if you develop fever, chills, flank pain, inability to urinate, or blood in the urine.

YOU WERE GIVEN A PRESCRIPTION FOR:
    TYLENOL #3 Tab 300-30MG
    MACROBID CAP100MG

YOU ARE REFERRED TO:
    Doctor Bebe T Newbirth
    Specializing in OB-GYN
    Office Telephone Number: (210) 555-1222
    Babies "R" Us
    1654 Lullabye Lane
    Suite #344
    San Antonio, TX 78202
Call for an appointment on 03/29/96.

YOU ARE REFERRED TO:
    Doctor Frank Garcia
    Specializing in Orthopedics
    Office Telephone Number: 222-2212
    Ortho S.M.A.R.T.
    7355 Barlite Blvd. #201
    San Antonio, TX. 78224
Call for an appointment on 04/02/96.

THANKS!
Thank you for choosing us for your medical needs. We hope you're satisfied with the care you received. If there was a problem, please call so we can "make things right."

Call at any time if you have questions concerning the treatment of your problem.

You should return at once if there is a significant worsening of your condition, or if any new symptoms arise.

If a follow-up examination was recommended for you, it's important that you be re-checked. If you encounter difficulty with your follow-up care, please call.

*Hospital Copy*    *Received By* _____    ©RLIS TeleMed

Southwest General Hospital
7400 Barlite Blvd. • San Antonio, TX 78224 • 210/921-3430
Physician Phone
Patient  Greta G Garbo
Address R x TYLENOL #3 TAB 300-30MG
    (Acetaminophen w/ Codeine Tab 300-30 MG)
    # 12 (Twelve)
    1 tab po q 3-4° as needed

---

Selection Permitted        Dispense As Written

Date  03/28/96     Dr. James Ross, Jr., MD
Refills None       DEA  AR1358212    State # H6940
©Medi-Span                                                    ©RLIS Telemed

---

Patient  Greta G Garbo
Doctor  James Ross, Jr., MD
Prescription for TYLENOL #3 TAB 300-30MG

GENERIC NAME: ACETAMINOPHEN (a-seat-a-MIN-oh-fen) and CODEINE (KOE-deen)

COMMON USES: This medicine is used to relieve pain.

HOW TO USE THIS MEDICINE: Follow the directions for using this medicine provided by your doctor. THIS MEDICINE MAY BE TAKEN WITH FOOD if it upsets your stomach. IF YOU MISS A DOSE OF THIS MEDICINE and you are using it regularly, take it as soon as possible. If it is almost time for your next dose, skip the missed dose and go back to your regular dosing schedule. Do not take 2 doses at once.

CAUTIONS: DO NOT EXCEED THE RECOMMENDED DOSE or take this medicine for longer than prescribed without checking with your doctor. Exceeding the recommended dose or taking this medicine for longer than prescribed may be habit-forming. THIS MEDICINE MAY CAUSE drowsiness or dizziness. Using this medicine alone, with other medicines, or with alcohol may lessen your ability to drive or to perform other potentially dangerous tasks. Ask your doctor or pharmacist if you have questions about which medicines cause drowsiness. BEFORE YOU BEGIN TAKING ANY NEW MEDICINE either prescription or over-the-counter, check with your doctor or pharmacist. This includes medicines which contain acetaminophen or antihistamines.

POSSIBLE SIDE EFFECTS: SIDE EFFECTS, that may go away during treatment, include dizziness, drowsiness, lightheadedness, constipation, nausea, or vomiting. If they continue or are bothersome, check with your doctor. CHECK WITH YOUR DOCTOR AS SOON AS POSSIBLE if you experience rash or itching. If you notice other effects not listed above, contact your doctor, nurse, or pharmacist.

©Medi-Span                                                    ©RLIS Telemed

While the invention has been described with reference to specific embodiments, modifications and variations of the invention may be constructed without departing from the scope of the invention, which is defined in the following claims.

We claim:

1. A medical records, documentation, tracking and order entry system, comprising at least one fault tolerant file server having at least one fault tolerant backup server, wherein the at least one file server has either standard hard drives or redundant array of independent drives, a software vendor, at least one communications server linked to the at least one file server for receiving incoming transcription and for remote reception of software, maintenance and system updates from the software vendor, a network having a hub and being connected to the file server, peripheral terminals connected to the network in a star configuration with the hub, the peripheral terminals having individual central processing units (CPUs), the CPUs having hard disks, touch screens, monitor, keyboards and mouses connected to the CPUs; software provided in the at least one communication server, in the at least one file server, and in the peripheral CPUs for receiving patient data in the peripheral CPUs via the touch screens, mouses, and keyboards and for storing the patient data in the peripheral CPUs and the at least one file server; and a distributed dictation system having inputs adjacent the CPUs, a transcription system for receiving and converting dictation from the inputs into transcribed dictations and the transcription system being connected to the at least one communication server for transmitting the transcribed dictations to the at least one communications server and an electronic storage bin connected to the at least one communication server for placing the transcribed dictations in the electronic storage bin and for transferring the transcribed dictations to the at least one file server, the electronic storage bin storing the transcribed dictations as text associated with the patient data for particular patients, printers connected to the network for printing reports on individual patients and system management reports of system operations, doctor related activities, nursing related activities and patient statistics.

2. A method of patient record documentation, tracking and order entry, comprising providing software in file servers, providing software from the file servers through a network hub and network to multiple peripheral CPUs, inputting data on data entry screens on monitors connected to the CPUs, the inputting comprising entering patient data in the multiple CPUs by touch screens, mouses and keyboards in response to the data entry screens on monitors connected to the CPUs, transferring the patient data from the CPUs to the file servers, making a record for individual patients, dictating portions of the record that are unique to particular patients, transmitting the dictation over lines to a transcription center, transcribing the dictation and transmitting the dictation transcriptions to at least one communication server, feeding the dictation transcriptions to the file servers as text, storing the text with the patient data on particular patients in the file servers, storing word and sentence generation and coordination software in the peripheral CPUs, generating text sentences in medical English text from patient data, displaying on the monitors connected to the peripheral CPUs the text sentences in medical English text combined with the text from the dictation transcriptions assembled as text summaries, and providing the text summaries from the peripheral CPUs to printers via the network for generation of printed patient textual reports.

3. The method of claim 2, further comprising installing utility software in the peripheral CPUs and generating management reports in the peripheral CPUs by calling the patient data over the network from the file servers and compiling the patient data as text and directing the compiled data to the printer.

4. The method of claim 2, further comprising producing nurses' notes data by entering the patient data with touch screens, mouses and keyboards, transferring the nurses' notes data from the peripheral CPUs to the file servers, storing the nurses' notes data in the file servers, transmitting the nurses' notes data to the peripheral CPUs, recompiling the nurses' notes data into nurses' notes text in the CPUs, displaying the nurses' notes text on peripheral CPU monitor screens, and printing the nurses' notes text on the printer.

5. The method of claim 2, further comprising storing prephrased text examples in the peripheral CPUs, and preliminarily inputting prephrased personalized text by individual physicians and nurses, and compiling the personalized text with the patient data for producing medical English text summaries and reports.

6. The method of claim 2, further comprising storing the text summaries in the peripheral CPUs, generating nurses' orders by entering physician orders to nurses with touch screens, mouses and keyboards at the peripheral CPUs, transmitting the physician orders as physician orders data to the file servers, storing physician orders data with the patient data in the file servers, providing the physician orders data with the patient data from the file servers to the peripheral CPUs, compiling the physicians' orders data, patient data and the stored text summaries, and displaying the physician orders data as textual nurses' orders on the displays, displaying all outstanding nurses' orders on the displays on request, displaying all nurses' orders specific to a patient on the display, entering executions of the nurses' orders on the display and automatically changing the executed nurses' orders to nurses' textual notes for display and printing in summaries.

* * * * *